United States Patent [19]
Brown

[11] Patent Number: 6,008,414
[45] Date of Patent: Dec. 28, 1999

[54] DIOXANE-MONOCHLOROBORANE AND DIOXANE-DICHLOROBORANE

[75] Inventor: Herbert C. Brown, West Lafayette, Ind.

[73] Assignee: Aldrich Chemical Company, Inc., Milwaukee, Wis.

[21] Appl. No.: 09/250,147

[22] Filed: Feb. 16, 1999

[51] Int. Cl.$^6$ .................................................. C07F 5/02
[52] U.S. Cl. .................................................. 568/6; 568/1
[58] Field of Search ............................................. 568/1, 6

[56] References Cited

U.S. PATENT DOCUMENTS 5,463,131  10/1995  Burkhart ...................... 569/1

OTHER PUBLICATIONS

CA:91:221686 abs of Inorg Chem by Hu 18(12) pp. 3297–3301, 1979.
CA:91:76290 abs of DE2740017, Mar. 1978.
CA:91:20568 abs of Inorg Chem by Dodds 18 (6) pp. 1465–1470, 1979.
CA:84:150687 abs of J Am Chem Soc by Brown 98(7) pp. 1785–1798, 1976.
CA:84:150688 abs of J Am Chem Soc by Brown 98(7) pp. 1798–1806, 1976.
CA:76:127050 abs of J Am Chem Soc by Brown 94 (6) pp. 2112–2113, 1972.
Chem abs accession No. 1999: 371602 by Brown in Organic Lett., 1999.

*Primary Examiner*—Gary Geist
*Assistant Examiner*—Jean F Vollano
*Attorney, Agent, or Firm*—Joyce R. Niblack

[57] ABSTRACT

Highly reactive hydroborating agents dioxane-monochloroborane and dioxane-dichloroborane are provided. Also provided by this invention are methods for producing dioxane-monochloroborane, dioxane-dichloroborane and methods for hydroborating olefins with these reagents.

8 Claims, No Drawings

DIOXANE-MONOCHLOROBORANE AND DIOXANE-DICHLOROBORANE

This invention relates to novel hydroboration reagents, dioxane-monochloroborane and dioxane-dichloroborane. These compounds are highly reactive hydroborating agents with exceptional properties. Hydroboration processes employing these new hydroborating agents and processes for producing dioxane-monochloroborane and dioxane-dichloroborane are also provided.

Hydroboration of alkenes using monochloroborane and dichloroborane provides anti-Markovnikov hydroboration products in >99.5% isomeric purity (Brown, H. C. et al. *J. Org. Chem.*, 1973, 38, 182. Brown, H. C. et al.; *J. Am. Chem. Soc.*, 1972, 94, 2112. Brown, H. C. et al.; *J. Org. Chem.*, 1977, 42, 2533. Brown, H. C. et al; *J. Am. Chem. Soc.*, 1976, 98, 1798.), unlike the simple borane reagents, such as $BH_3$:THF and $BH_3$:DMS, which give a mixture of regioisomers (Brown, H. C. et al.; *J. Am. Chem. Soc.* 1959, 81, 6428. Brown, H. C. et. al.; *J. Am. Chem. Soc.*, 1960, 82, 4708. Brown, H. C., Organic Synthesis via Boranes: Wiley, N.Y., 1975. A reprinted edition is currently available: Organic Synthesis via Boranes; Aldrich Chemical Co., Inc.: Milwaukee, Wis. 1997; Vol 1.). Alkylchloroboranes are widely used for many synthetic transformations. For example, dicyclohexylchloroborane has been used as an enolizing agent for aldol type reactions (Brown H. C. et al.; *J. Org. Chem.*, 1992, 57, 499.), while (+)- or (−)-$Ipc_2BCl$ and $Eap_2BCl$ reveal promising characteristics as chiral reducing agents (Brown, H. C. et al.; *J. Am. Chem. Soc.*, 1988, 110, 1539. Brown, H. C. et al; *Tet. Lett*, 1991, 32, 6691. Ramachandran, P. V.; and Brown, H. C. In 'Reductions in Organic Synthesis' A. F. Abdel-Magid Ed., American Chemical Society, Washington D.C., 1996, Chapter 5). Similarly, alkyldichloroboranes are used in the synthesis of carboxylic acids and amines from olefins (Brown H. C. et al.; *J. Am. Chem. Soc.*, 1973, 95, 2394. Midland M. M. and Brown H. C., *J. Am. Chem. Soc.*, 1973, 95, 4069.). The current monochloroborane and dichloroborane adducts, such as dimethyl sulfide:$BH_2Cl$, dimethyl sulfide:$BHCl_2$, diethyl ether:$BH_2Cl$ and diethyl ether:$BHCl_2$ serves major needs in these applications. However, these reagents do suffer from some disadvantages. The dimethyl sulfide:$BH_2Cl$ is a stable reactive adduct, but exists in equilibrium with dimethyl sulfide:$BH_3$ (12.5%) and dimethyl sulfide:$BHCl_2$ (12.5%). The dimethyl sulfide:$BHCl_2$ can be obtained in 95% pure form. However, this adduct is unreactive towards olefins at room temperature and needs the addition of 1 equiv. of $BCl_3$ to achieve the hydroborations. Also, the unpleasant odor of dimethyl sulfide poses environmental problems in large scale operations. The diethyl ether:$BH_2Cl$ and diethyl ether:$BHCl_2$ adducts are free from these problems and can be obtained in almost 90% and 98% purities respectively. However, these reagents are unstable, can be prepared only in 1 M solutions and must be freshly prepared before reaction (Brown H. C. et al., Polish J. Appl. Chem., 1983, 26, 155.). The adduct, tetrahydrofuran-$BH_2Cl$, can be obtained in 98% purity; however, its low reactivity limits its applications. (ibid). The increasing use of these chloroborane reagents and the diverse applications of the product dialkylchloroboranes and monoalkylchloroborane in organic synthesis prompted us to investigate the possibilities of providing a more convenient reagent for these applications. This invention provides new, highly pure, reactive dioxane:$BH_2Cl$ and dioxane:$BH_2Cl$ adducts for such applications.

SUMMARY OF THE DISCLOSURE

The new, highly reactive hydroborating agents, monochloroborane:dioxane and dichloro-borane:dioxane are disclosed along with their preparation and hydroboration processes employing these new reagents.

DISCLOSURE OF PREFERRED EMBODIMENTS

Dioxane:$BCl_3$ was prepared by passing $BCl_3$ gas slowly into dioxane at 0° C. The adduct thus obtained is a solid which melts at 56° C. (with decomposition), but is stable at 0° C. for several weeks. Reaction of this adduct with diborane in dioxane produces dioxane-$BH_2Cl$ as outlined in the following equation.

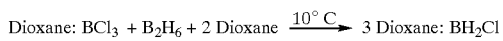

The dioxane:$BH_2Cl$ adduct thus obtained was 98% pure by $^{11}B$ NMR (+7.9, triplet). The adduct is a liquid, 6.2 M in $BH_2Cl$, with a hydrogen to chlorine ratio of 2.00:1.00. The stability of this adduct at 0° C. and room temperature (25° C.) was monitored using $^{11}B$ NMR examination of a sealed sample (2 M dioxane:$BH_2Cl$ in dioxane) in an NMR tube, recording the $^{11}B$ NMR at intervals. It was also checked using active hydride analysis. Both of these studies did not show any detectable change over a period of six months.

The reaction of dioxane:$BCl_3$ with appropriate amounts of diborane in presence of dioxane also produced dioxane:B-$HCl_2$ as outlined in the following equation.

The dioxane:$BHCl_2$ adduct thus obtained was >99% pure by $^{11}B$ NMR (+8.2, doublet). The adduct is liquid at 0° C., 5.8 M in $BHCl_2$, with a hydrogen to chlorine ratio of 1.00:2.00. The stability of this adduct at 0° C. was monitored using $^{11}B$ NMR examination of a sealed sample (2 M dioxane:$BH_2Cl$ in dioxane) in an NMR tube, recording the $^{11}B$ NMR at intervals. It was also checked using active hydride analysis. Both of these studies did not show any detectable change over a period of six months. However, at room temperature small amounts (2–5%) of dioxane cleaved products were formed after 3 months.

An alternate synthesis route employs $NaBH_4$ (10% excess), and dioxane:$BCl_3$ and 3% (by vol.) of triglyme. It is essential to add small catalytic amounts of triglyme (or an equivalent amount of diglyme, tetraglyme or polyglyme). Decantation of the clear supernatant layer, provided dioxane:$BH_2Cl$ of 98% purity or dioxane:$BHCl_2$ of >99% purity depending on the amount of $NaBH_4$ employed.

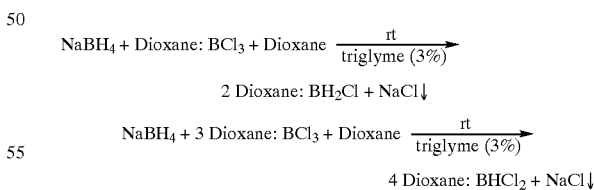

Interestingly, the $^1H$ NMR spectrum in $CDCl_3$ of dioxane:$BH_2Cl$ and dioxane:$BHCl_2$ thus obtained did not show the presence of triglyme. It is apparently absorbed by the precipitated sodium chloride. The mono- and dichloroborane adducts thus obtained (6.3 M and 5.8 M respectively) are stable for long periods at 0° C. as well as at room temperature.

To establish the reactivity of these new adducts towards representative olefins, hydroboration studies using dioxane:BH$_2$Cl and dioxane:BHCl$_2$ were carried out in dioxane and in dichloromethane solvents.

The hydroborations studies using dioxane:BH$_2$Cl were carried out by the addition of an olefin in dioxane or dichloromethane to dioxane:BH$_2$Cl at 0° C., followed by further stirring as the reaction mixture was brought to room temperature. The final solution was 0.5 M in BH$_2$Cl and 1M in the olefin. Representative olefins such as 1-decene, 2-methyl-1-pentene, cis-4-methyl-2-pentene, 2-methyl-2-butene, β-pinene, cyclohexene, α-pinene, 3-carene, 1-phenyl-2-methyl-1-propene, 2,3-dimethyl-2-butene and 1,2-dimethylcyclopentene were utilized. The progress of these hydroboration reactions were monitored by $^{11}$B NMR and hydride analysis of the residual active hydride present by removing aliquots at intervals and measuring the hydrogen evolved by injecting them into a glycerin-water mixture. The mono-, di- and some trisubstituted olefins were hydroborated rapidly to the corresponding dialkylchloroborane stage within 0.5 h. The more hindered olefins were rapidly hydroborated to the monoalkyl stage, with further hydroboration proceeding slowly. The results were presented in Table 1.

In the hydroboration of less hindered olefins using dioxane:BH$_2$Cl, only the corresponding dialkylchloroboranes were obtained as observed by $^{11}$B NMR (~+75 ppm). Methanolysis of these products gave B-methoxydialkylboranes cleanly (~+54 ppm). However, in the hydroboration of more hindered olefins such as 2,3-dimethyl-2-butene and 1,2-dimethylcyclopentene, considerable amounts of the monoalkylchloroboranes were also formed.

TABLE 1

Hydroboration of Representative Olefins Using Dioxane-BH$_2$Cl in Dioxane and Dichloromethane at Room Temperature[a]

| Olefin | Reaction time (h) in dioxane | Hydride used[b] (equiv) | Reaction time (h) in dichloromethane | Hydride used[b] (equiv) |
|---|---|---|---|---|
| 1-decene | 0.25 | 2.00 | 0.25 | 2.00 |
| 2-methyl-1-pentene | 0.25 | 2.00 | 0.25 | 2.00 |
| cis-4-methyl-2-pentene | 0.25 | 2.00 | 0.25 | 2.00 |
| 2-methyl-2-butene | 0.50 | 2.00 | 0.50 | 2.00 |
| β-pinene | 0.25 | 2.00 | 0.25 | 2.00 |
| cyclohexene | 0.50 | 2.00 | 0.50 | 2.00 |
| 3-carene | 0.50 | 2.00 | 1.0 | 2.00 |
| α-pinene | 0.50 | 1.92 | 0.50 | 1.82 |
|  | 1.0 | 2.00 | 1.50 | 2.00 |
| 2-methyl-1-phenyl-1-propene | 0.25 | 1.00 | 0.50 | 1.00 |
|  | 4.0 | 1.82 | 4.0 | 1.76 |
| 2,3-dimethyl-2-butene | 0.25 | 1.18 | 0.50 | 1.18 |
|  | 48.0 | 1.76 | 48.0 | 1.68 |
| 1,2-dimethyl-cyclopentene | 0.50 | 1.00 | 0.50 | 1.00 |
|  | 48.0 | 1.62 | 48.0 | 1.54 |

[a]All reactions were carried out in solutions of dioxane or dichloromethane which were 1.0M in olefin and 0.50M in BH$_2$Cl (the olefin was used in small excess (5%)).
[b]Hydride analysis was carried out by hydrolyzing an aliquot with a 1:1 mixture of glycerol:water and measuring the hydrogen evolved.

Similarly, hydroboration studies of representative olefins, such as 1-octene, 1-decene, 2-methyl-1-butene, 2-methyl-1-octene, cis-4methyl-2-pentene, 2-methyl-2-butene, methylenecyclopentane, β-pinene, camphene, cyclohexene, α-pinene, 3-carene, 1-phenyl-2-methyl-1-propene, 2,3-dimethyl-2-butene and 1,2-dimethylcyclopentene with dioxane:BH$_2$Cl were carried out in dichloromethane. Interestingly, dioxane:BHCl$_2$ showed exceptional selectivities in such hydroborations. The hydroboration of 2-disubstituted-1-enes using dioxane:BHCl$_2$ is very fast giving exclusively RBCl$_2$, where as other terminal olefins (for example, 1-decene, 1-octene etc.,) or hindered olefins (for example, cyclohexene, α-pinene etc) took longer hours and gave mixture of products (RBCl$_2$, R$_2$BCl and BCl$_3$).

The following Table 2 summarizes the results.

TABLE 2

Hydroboration of Representative Olefins Using Dioxane:BHCl$_2$ in Dichloromethane at Room Temperature.[a]

| Olefin | Reaction Time (h) | Amount (in %) of RBCl$_2$[b] | Amount (in %) of BCl$_3$[b] | Amount (in %) of R$_2$BCl[b] |
|---|---|---|---|---|
| 1-Octene | 24 | 30 | 60 | 10 |
| 1-Decene | 24 | 28 | 60 | 12 |
| 2-Methyl-1-butene | 1 | 95 | 2 | 3 |
| 2-Methyl-1-octene | 1 | 95 | 2 | 3 |
| Methylenecyclopentane | 1.5 | 92 | 4 | 3 |
| β-Pinene | 1.5 | 94 | 4 | 2 |
| Camphene | 36 | 92 | 4 | 3 |
| cis-4-Methyl-2-pentene | | Very slow reaction | | |
| Cyclohexene | | Very slow reaction | | |
| 2-Carene | | No significant hydroboration | | |
| α-Pinene | | No significant hydroboration | | |
| 2,3-Dimethyl-2-butene | | No significant hydroboration | | |
| 1,2-Dimethyl-cyclopentene | | No significant hydroboration | | |

[a]Hydroborations were carried out by the addition of an olefin to dioxane; BHCl$_2$ in dichloromethane at 0° C. and further stirred at room temperature. The final solution is 1.00M in an olefin and 1.00M in BHCl$_2$.
[b]Amounts obtained from $^{11}$B NMR analysis of the methanolized product.

It is clearly evident from the above Table 2 that the 2-substituted-1-enes, such as 2-methyl-1-butene, 2-methyl-1-octene, methylenecyclopentane, β-pinene and camphene are cleanly hydroborated to RBCl$_2$ stage whereas other classes of olefins are hydroborated sluggishly. These hydroborations can be carried out conveniently by using an additional equivalent of BCl$_3$ as in the case of dimethyl sulfide:BHCl$_2$ (Brown H. C. et al., *J. Org. Chem.*, 1977, 42, 2533.)

The unusual reactivity of dioxane:BHCl$_2$ towards 2-substituted-1-enes was used for selective hydroboration of terminal double bond of limonene leaving the internal double bond unaffected as shown in the following scheme.

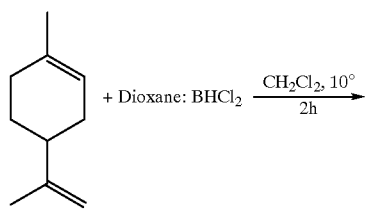

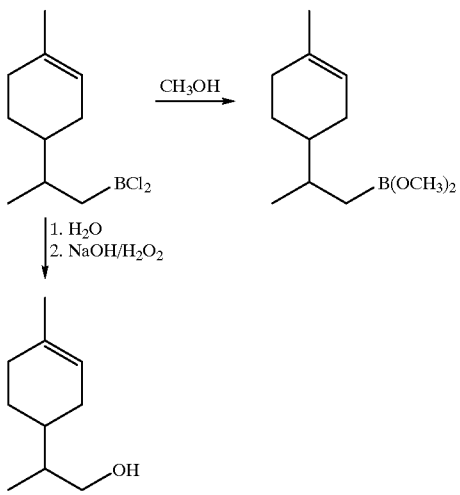

DETAILED DESCRIPTION OF PREFERRED EMBODIMENTS

The following examples further illustrate the present invention. All handling and reactions with air-sensitive compounds were carried out in an atmosphere of dry nitrogen. The special techniques employed in handling air sensitive compounds is described in Brown H. C., Organic Synthesis via Boranes, Wiley, N.Y., 1975, Chapter 9, p191–261 (A reprinted edition is currently available: Organic Synthesis via Boranes; Alrich Chemical Co., Inc.: Milwaukee, Wis. 1997; Vol 1). All glassware was dried overnight in an oven, assembled hot, and cooled to ambient temperature in a stream of nitrogen. $^{11}B$ NMR spectra were recorded on a Varian Gemini 300 MHz instrument. The GC analyses were carried out on Varian-3000 gaschromatograph provided with FID using Carbowax-20 column. The $^{11}B$ NMR chemical shifts, $\delta$, are in ppm relative. to $BF_3:OEt_2$. Diborane generation procedure and hydride analysis studies carried out using hydrolysis to hydrogen, followed by measurement of the hydrogen evolved with a gasimeter, are described in Brown H. C., Organic Synthesis via Boranes (ibid.). All the procedures described below can be scaled-up without any difficulties.

EXAMPLE 1

Preparation of dioxane:$BH_2Cl$

An oven-dried 100 mL round-bottom flask provided with magnetic pellet, septum inlet, gas inlet, a condenser whose end was connected to a mercury bubbler, was cooled to 10° C. under stream of dry nitrogen. The flask was charged with dioxane:$BCl_3$ (21.33 g, 100 mmol) in dioxane (19.24 g, 110 mmol). The diborane gas (110 mmol) was bubbled slowly into dioxane:$BCl_3$ in dioxane through a sintered tip gas bubbler during 2 h. The contents were further stirred at 10° C. for another 1h, by which time the $^{11}B$ NMR examination of the reaction mixture showed clean formation of dioxane:$BH_2Cl$ (+7.9, triplet, 98%) and disappearance of peak due to dioxane:$BCl_3$ (+11.8, singlet).

EXAMPLE 2

Preparation of dioxane:$BHCl_2$

An oven-dried 100 mL round-bottom flask provided with magnetic stirring bar, septum inlet, gas inlet, a condenser whose end was connected to a mercury bubbler, was cooled to 10° C. under stream of dry nitrogen. The flask was charged with dioxane:$BCl_3$ (42.67 g, 200 mmol) in dioxane (9.62 g, 100 mmol). The diborane gas (55 mmol) was bubbled slowly into dioxane:$BCl_3$ in dioxane through a sintered tip gas bubbler during 2 h. The contents were further stirred at 10° C. for another 1 h, by which time the $^{11}B$ NMR examination of the reaction mixture showed clean formation of dioxane:$BHCl_2$ (+8.2, triplet) and disappearance of peak due to dioxane:$BCl_3$ (+11.7, singlet).

EXAMPLE 3

Preparation of dioxane:$BH_2Cl$ by the reaction of $NaBH_4$ with dioxane:$BCl_3$ in dioxane An-oven dried 100 mL round-bottom flask provided with magnetic stirring bar, septum inlet was cooled to 10° C. and flask was charged with $NaBH_4$ (7.92 g, 220 mmol). To this was added dioxane:$BCl_3$(42.67 g, 200 mmol) in dioxane (19.22 g, 200 mmol) and the contents were stirred for 10 minutes. Triglyme (1.5 mL, 9 mmol, 3% by vol.) was added to the reaction mixture and the contents were further stirred at room temperature for 36 h. The contents were allowed to settle (can be centrifuged for quantitative precipitation of sodium chloride formed) and the clear supernatant liquid was decanted under nitrogen. The $^{11}B$ NMR examination showed clean formation of dioxane:$BH_2Cl$ (+7.8, triplet, 98%)

EXAMPLE 4

Preparation of dioxane:$BHCl_2$ by the reaction of $NaBH_4$ with dioxane:$BCl_3$ in dioxane An oven-dried 100 mL round-bottom flask provided with magnetic stirring bar, septum inlet was cooled to 10° C. and flask was charged with dioxane:$BCl_3$ (64.00 g, 300 mmol) in dioxane (9.62 g, 100 mmol). To this was added $NaBH_4$ (3.96 g, 110 mmol) and the contents were stirred for 10 minutes. Triglyme (1.5 mL, 9 mmol, 3% by vol.) was added to the reaction mixture and the contents were further stirred at room temperature for 36 h. The contents were allowed to settle (can be centrifuged for quantitative precipitation of sodium chloride formed) and the clear supernatant liquid was decanted under nitrogen. The $^{11}B$ NMR examination showed clean formation of dioxane:$BHCl_2$ (+8.2, doublet, >99%)

EXAMPLE 5

Hydroboration of representative olefins with dioxane:$BH_2Cl$

Hydroboration of representative olefins, such as 1-decene, 2-methyl-1-pentene, cis-4-methyl-2-pentene, 2-methyl-2-butene, β-pinene, cyclohexene, α-pinene, 3-carene, 1-phenyl-2-methyl-1-propene, 2,3-dimethyl-2-butene and 1,2-dimethylcyclopentene with dioxane:$BH_2Cl$ were carried out in dioxane and dichloromethane solvents. The procedure followed for all the olefins in both the solvents are same. The procedure followed for 1-decene in dichloromethane is representative.

An oven-dried 50 mL round-bottom flask provided with septum inlet and stirring bar was cooled to 0° C. under nitrogen. The flask was charged with dioxane:$BH_2Cl$ in dichloromethane (8.7 mL, 5 mmol). To this was added 1-decene (1.4 g, 10 mmol). The final solution is 0.5 M in $BH_2Cl$ and in 1-decene. The contents were further stirred at room temperature. The course of the reaction was followed by $^{11}B$ NMR and hydride analysis of residual active hydride. Both of these studies showed completion of the reaction after 15 min.

$^{11}B$ NMR after 15 min: +75 (broad singlet), 52 (singlet, after methanolysis).

Hydride analysis after 15 min: no active hydride present.

The reaction mixture was treated with slow addition of water followed by the addition of sodium hydroxide (7.0 m , 3 M, 21 mmol). Hydrogen peroxide (6 mmol) was added slowly and contents were further stirred at room temperature (3 h) and 40° C. (1 h) to ensure complete oxidation. The organic compound was extracted into diethyl ether. Drying and evaporation of the solvent provided essentially pure 1-decanol in 98% yield by GC); isolated 1.48 g, 95% yield. The GC analysis showed only 0.05% of 2-decanol.

EXAMPLE 6

Hydroboration of representative olefins with dioxane:$BHC_2$

Hydroboration of representative olefins, such as 1-octene, 1-decene, 2-methyl-1-butene, 2-methyl-1-octene, cis-4-methyl-2-pentene, 2-methyl-2-butene, methylenecyclopentane, β-pinene, camphene, cyclohexene, α-pinene, 3-carene, 1-phenyl-2-methyl-1-propene, 2,3dimethyl-2-butene and 1,2-dimethylcyclopentene with dioxane:$BH_2Cl$ were carried out in dioxane and dichloromethane solvents. The hydroboration were rapid and complete only for 2-substituted-1-enes, such as 2-methyl-1-butene, 2-methyl-1-octene, methylenecyclopentane, β-pinene and camphene. The hydroboration of other olefins is sluggish at room temperature. The procedure followed for all the olefins in both the solvents are same. The procedure followed for β-pinene in dichloromethane is representative.

An oven-dried 50 mL round-bottom flask provided with septum inlet and stirring bar was cooled to 0° C. under nitrogen. The flask was charged with dioxane:$BHCl_2$ in dichloromethane (7.5 mL, 10 mmol). To this was added β-pinene (1.37 g, 10 mmol). The final solution is 1 M in $BHCl_2$ and 1.0 M in β-pinene. The contents were further stirred at room temperature. The course of the reaction was followed by $^{11}B$ NMR and hydride analysis of residual active hydride. Both of these studies showed completion of the reaction after 1.5 h $^{11}B$ NMR after 1.5 h: +16.9 (broad singlet). +31.5 (singlet, after methanolysis).

Hydride analysis after 1.5 h: no active hydride present.

The reaction mixture was treated with slow addition of water followed by the addition of sodium hydroxide (10.0 mL, 3 M, 30 mmol). Hydrogen peroxide (12 mmol) was added slowly and the contents were further stirred at room temperature (3 h) and 40° C. (1 h) to ensure complete oxidation. The organic compound was extracted into diethyl ether. Drying and evaporation of the solvent provided essentially pure myrtanol in 97% yield (by GC); isolated 1.37 g, 91% yield.

EXAMPLE 7

Selective hydroboration of limonene using dioxane:$BHCl_2$

An oven-dried 50 mL round-bottom flask provided with septum inlet and stirring bar was cooled to 0° C. under nitrogen. The flask was charged with dioxane:$BHCl_4$ in dichloromethane (7.5 mL, 10 mmol). To this was added limonene (1.36 g, 10 mmol). The final solution is 1 M in $BHCl_2$ and 1.0 M in limonene. The contents were further stirred at room temperature. The course of the reaction was followed by $^{11}B$ NMR and hydride analysis of residual active hydride. Both of these studies showed completion of the reaction after 2 h.

$^{11}B$ NMR after 2 h: +17.3 (broad singlet). +31.5 (singlet, after methanolysis).

Hydride analysis after 2 h: no active hydride present

The reaction mixture was treated with slow addition of water followed by the addition of sodium hydroxide (10.0 mL, 3 M, 30 mmol). Hydrogen peroxide (12 mmol) was added slowly and the contents were further stirred at room temperature (3 h) and 40° C. (1 h) to ensure complete oxidation. The organic compound was extracted into diethyl ether. Drying and evaporation of the solvent provided essentially pure p-menth-1-en-9-ol in 90% yield (1.35 g). The GC analysis did not show any signal corresponding to the diol. The spectral data matched with the commercial sample.

I claim:

1. A hydroborating agent selected from the group consisting of dioxane-chloroborane and dioxane-dichloroborane.

2. A hydroborating agent: dioxane-monochloroborane.

3. A hydroborating agent: dioxane-dichloroborane.

4. A process for hydroborating olefins to the corresponding alkylchloroborane comprising the step of reacting a hydroborating agent selected from the group consisting of dioxane-monochloroborane and dioxane-dichloroborane with an olefin.

5. A process in accordance with claim 4 wherein the hydroborating agent is dioxane-monochloroborane.

6. A process in accordance with claim 4 wherein the hydroborating agent is dioxane-dichloroborane.

7. A process in accordance with claim 4 wherein the hydroborating agent is dioxane-monochloroborane which is prepared by reacting dioxane-boron trichloride with diborane in dioxane.

8. A process in accordance with claim 4 wherein the hydroborating agent is dioxane-dichloroborane which is prepared by reacting dioxane-boron trichloride in dioxane with sodium borohydride in the presence of catalytic amounts of a glyme selected from the group consisting of diglyme, triglyme, tetraglyme and polyglyme.

* * * * *